United States Patent [19]
DeYoe et al.

[11] Patent Number: 5,339,813
[45] Date of Patent: Aug. 23, 1994

[54] PATIENT VIDEO SYSTEM FOR MEDICAL IMAGING EQUIPMENT

[75] Inventors: Edgar A. DeYoe, Delafield; John F. Neitz, New Berlin, both of Wis.

[73] Assignee: The MCW Research Foundation, Inc., Milwaukee, Wis.

[21] Appl. No.: 103,937

[22] Filed: Aug. 6, 1993

[51] Int. Cl.5 ............................................. A61B 6/00
[52] U.S. Cl. ........................... 128/653.1; 128/653.5; 378/204; 359/419; 359/894
[58] Field of Search ............... 128/653.2, 653.5, 653.1; 324/318, 322; 359/418–434, 894; 33/246; 356/251, 252; 378/204

[56] References Cited

U.S. PATENT DOCUMENTS

| | | | |
|---|---|---|---|
| 4,901,141 | 2/1990 | Costello | 128/653.2 X |
| 5,076,275 | 12/1991 | Bechor et al. | 128/653.2 |
| 5,134,373 | 7/1992 | Tsuruno et al. | 128/653.5 X |

FOREIGN PATENT DOCUMENTS 4303420 10/1992 Japan ........................... 128/653.2

*Primary Examiner*—Ruth S. Smith
*Attorney, Agent, or Firm*—Quarles & Brady

[57] ABSTRACT

A video system for use by a patient positioned in the bore of an MRI scanner includes a scope through which the patient can view a remote target area while a scan is being performed. A liquid crystal display system produces a color image at the target area which can be manipulated with a computer to perform MRI brain function experiments or tests.

9 Claims, 3 Drawing Sheets

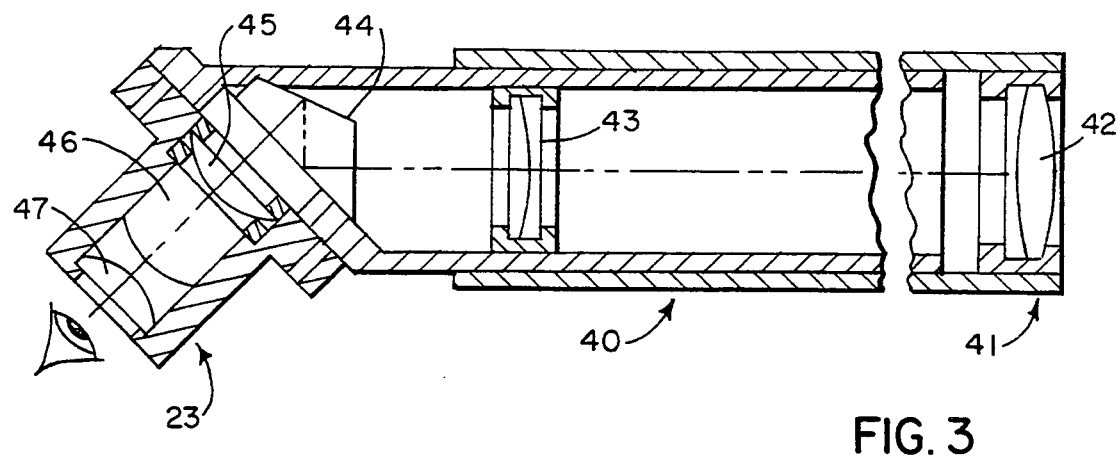
FIG. 3
FIG. 4
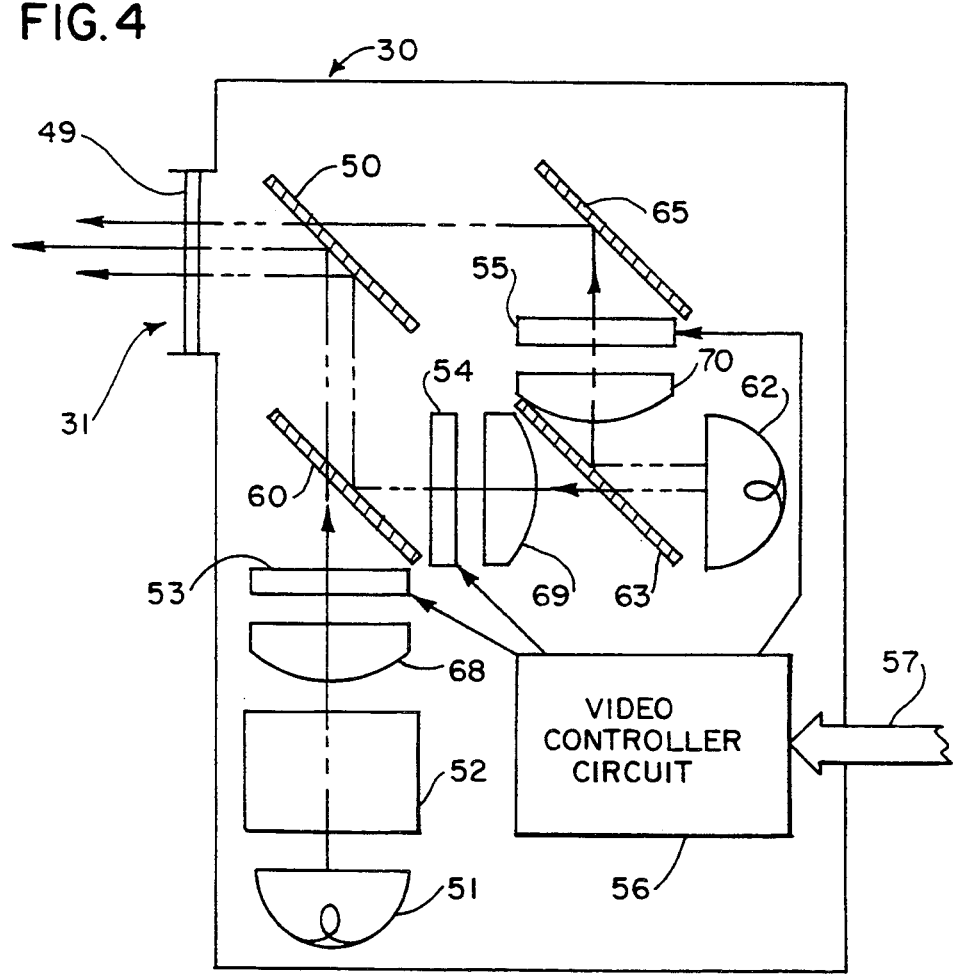

PATIENT VIDEO SYSTEM FOR MEDICAL IMAGING EQUIPMENT

BACKGROUND OF THE INVENTION

The field of the invention is the projection of video and computer generated images to a patient positioned within medical imaging systems such as MRI or PET scanners.

Positron emission tomographic (PET) scanners have been used for many years to produce images which show areas of the brain that are active while the subject performs specific functions or is stimulated by sight, sound, smell or touch. More recently, as described in co-pending U.S. patent application Ser. No. 08/005,723 entitled "Time Course MRI Imaging Of Brain Functions", similar images are now produced with magnetic resonance imagers (MRI). In both cases the apparatus required to visually stimulate the subject must operate under severe conditions due to the environments in which they are used. In the case of MRI, for example, the subject's head may be positioned in the very confined opening of a head coil and the apparatus is subjected to very intense magnetic fields (i.e. 0.5 to 3.0 Tesla). As a result, the video apparatus must feed the visual information to the patient and it must not contain any ferromagnetic materials. Indeed, because of the rapidly switched magnetic field gradients required in MRI, no conductive material can be used because such materials will support Eddy currents that distort the magnetic fields required for accurate imaging.

To study the brain it is necessary to stimulate the subject with a wide range of colors and brightnesses that can be accurately controlled. In addition, it requires that the subject be stimulated over a wide field of view and that three dimensional images be presented. For example, a field of view of 15°, typical of commercially available binoculars, stimulates on 25% to 30% of the brain areas associated with vision, whereas a field of view of 60° stimulates 80% to 85% of these areas.

SUMMARY OF THE INVENTION

The present invention relates to a system for visually stimulating a subject positioned in the bore of a medical imaging device such as an MRI scanner. More particularly, the system includes a pair of scopes, each having an objective lens mounted at one end of a barrel assembly for receiving light from an image and an eyepiece mounted at the other end of the barrel assembly; means for mounting the pair of scopes such that their eyepieces engage the respective eyes of a subject positioned in the bore of a medical imaging device and aim the scopes toward a target area located remotely from the medical imaging device; and a display system located remotely from the medical imaging device and being operable to produce and display an image in the target area. The scopes are characterized by a very high magnification factor, a design that enables focusing on nearby objects, a compact length and a focal point for each eyepiece which focuses all incoming light to a focal point smaller than the subject's constricted pupil as the light enters the eye. The display system is characterized by the use of liquid crystal displays ("LCD") for each of the primary colors to enable very bright images with accurate colors to be produced.

A general object of the invention is to provide a visual display for a subject positioned within the bore of a medical imaging device. The scopes are made of non-metallic and non-ferromagnetic materials which will not interfere with the operation of the imaging device. Through the appropriate use of prisms to bend the light paths, the scopes may be shaped to reach the subject's eyes even in very confined imaging procedures. The display system is located remotely from the imager such that it is not affected by strong magnetic fields or radiation associated with the imaging modality.

Another object of the invention is to provide images over a very wide field of view so as to enable stimulation of a large portion of the subject's brain. In addition to providing more life-like and entertaining images, the wide field of view is necessary to conduct research and tests on all parts of the brain associated with vision.

Yet another object of the invention is to provide images in which the color and brightness can be accurately controlled over a wide range of values. By employing separate liquid crystal displays for each of the three primary colors and combining the resulting three monochromatic images into a single color image, the display system can provide a much wider range of colors and brightnesses than other display devices such as cathode ray tubes. In addition, color and brightness can be accurately controlled so that the response of the brain to color and brightness can be measured with accuracy. Also, because the light is focused to a small focal point as it enters the eye, the intensity of the light reaching the retina is not affected by variations in pupil dilation.

Yet another object of the invention is to enable conventional display system technologies to be used. Because the display system is located remotely from the imager, no special precautions are required to protect its circuitry and other components from high magnetic fields or radiation. As a result, images can be brought to the subject using relatively low cost equipment.

Another object of the invention is to correct for variations in a patient's vision so that clear and sharp images are seen. Normal eyeglasses cannot be worn in medical imagers such as MRI scanners because they contain metal components. The present invention enables correction for refractive errors (and to some extent astigmatism) so that clear images can be displayed without the use of eyeglasses.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

FIG. 3 is a view in cross section through one of the scopes that forms part of the invention shown in FIGS. 1 and 2;

FIG. 4 is a schematic diagram of a display system which forms part of the invention shown in FIG. 1.

DESCRIPTION OF THE PREFERRED EMBODIMENT

Figure 1:
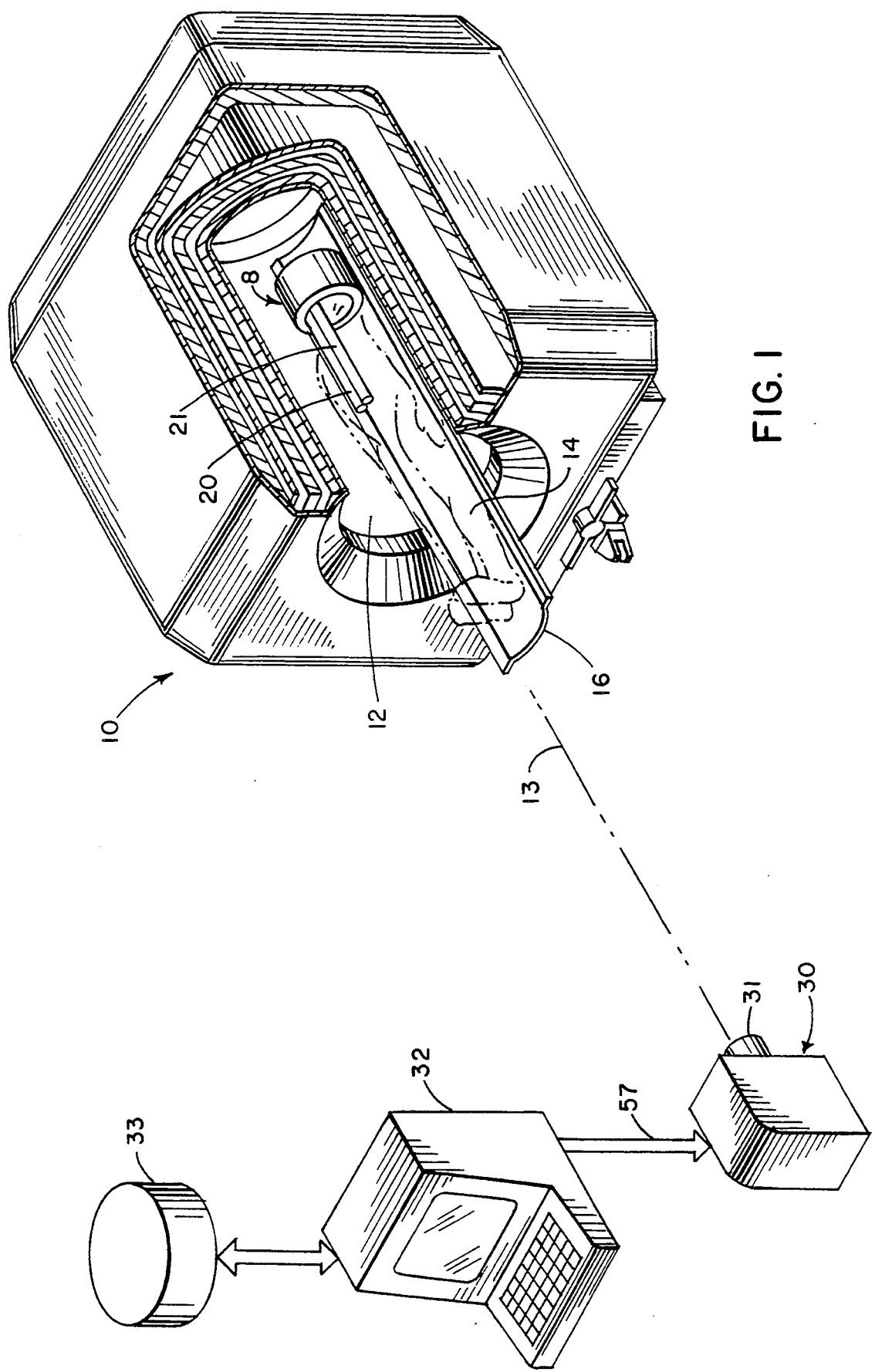
FIG. 1 is a perspective view with parts cut away of an MRI scanner in which the present invention is employed.

Referring particularly to FIG. 1, an MRI magnet assembly 10 has a cylindrical bore tube 12 extending along an axis 13 for receiving a supine patient 14 supported on a table 16. The table 16 is moved in and out of the bore tube 12 to position the patient 14 along the axis 13 within the volume of the bore tube 12.

Surrounding the bore tube 12 and patient 14 are a number of coils which produce the polarizing, gradient and excitation magnetic fields required for MRI. Typically, a superconducting magnet is employed to produce the polarizing magnetic field and it may have a strength ranging from 0.5 to 3.0 Tesla. Because of this enormous magnetic field, the magnet assembly 10 is housed in a special room (or trailer in the case of portable units) and many precautions are taken to keep ferromagnetic materials away from the assembly 10. For example, in a 1.5 Tesla installation ferromagnetic materials and items sensitive to magnetic fields are maintained at least sixteen feet away from the magnet assembly 10. Also, the magnetic field gradients produced by the magnet assembly 10 are switched at relatively high frequencies and induce Eddy currents in any conductive material within the bore tube 12. Such Eddy currents produce heat and they distort the homogeneous magnetic fields required for proper imaging.

While MRI images are typically produced using coils disposed around the bore tube 12, when MRI imaging of brain functions is performed a local coil assembly 8 such as that described in co-pending U.S. patent application Ser. No. 08/006,219 and entitled "NMR Local Coil For Brain Imaging" is employed. Such local head coils are cylindrical in shape, and as shown best in FIG. 2, they encircle the patient's head with minimal clearance. The tightly fitted head coils are required to improve the signal-to-noise ratio of the NMR signals sufficiently to produce meaningful images.

The present invention is comprised in part of a pair of scopes 20 and 21 which are mounted to the local coil assembly 8 and positioned with their eyepieces 23 against the eyes of the patient 14. The scopes 20 and 21 are aimed along the bore axis 13 at a target area located remotely from the magnet assembly 10. As shogun best in FIG. 2, the scopes 20 and 21 pass between the patient's face and the closely surrounding head coil 8 and they extend a substantial distance along the length of the bore tube 12. As will be explained in more detail below, this length is necessary to obtain the high magnification at relatively close focusing distances required for this application.

Referring particularly to FIG. 1, a display system 30 is positioned in the target area of the scopes 20 and 21. This location is at least sixteen feet from the magnet assembly 10 so that conventional electronic and optical technologies can be employed without damage or image distortion from the high magnetic fields. As will be described in more detail below, a model XG-2000u LCD video projector commercially available from Sharp Corporation, Osaka, Japan has been modified for this purpose. The display system 30 produces a 2"×2" color image at a front opening 31 in response to a conventional RGB video signal received from a computer 32. The computer 32 receives the image data from disc storage 33, and in brain function experiments, a sequence of images may be played out in a repetitive pattern. The two inch square image produced by the display 30 is magnified by the scopes 20 and 21 to form an image which fills approximately 60° of the patient's field of view. While the color LCD display is preferred for brain function imaging, other displays may also be employed, particularly when the primary purpose is to entertain the patient and provide a pleasant distraction from an otherwise confining experience. In such applications, the video signal may be produced from an NTSC or S-video source, such as a commercially available VCR.

Referring particularly to FIG. 3, the scopes 20 and 21 are identical in construction and performance. Each includes a two piece tube assembly 40 which mounts at one end, an eyepiece assembly 23 and at its other end an objective lens assembly 41. The objective lens assembly 41 supports an objective lens 42 which is an achromatic doublet, convex lens that has a focal length $f_0 = 400$ mm and in conjunction with the concave lens described below provides the required magnification of approximately 100. An achromatic doublet, concave lens 43 of focal length $f_0 = -46$ mm is mounted in the tube assembly 40 and it enables the length of the scopes 20 and 21 to be reduced significantly compared to telescope designs that do not employ a "negative" lens. A prism 44 bends the light path downward at an angle of 45° into the eyepiece assembly 23. The eyepiece assembly 23 includes a compound field lens comprised of elements 45 and 46 and an eye lens 47. The eyepiece assembly 23 has an effective focal length of 20 millimeters, which is the typical distance between the eye lens 47 and the pupil of the patient's eye. By focusing the image at the pupil, all of the light passes into the eye even when the iris is fully constricted. This ensures that a bright image is seen over a wide field of view. Also since the light passes through a very small portion of the cornea, patient astigmatism will have very little effect on image quality except in the most extreme cases. Consequently, differences between patients may be accommodated by sliding the objective lens 42 in or out until the image is brought into sharp focus.

Figure 5:
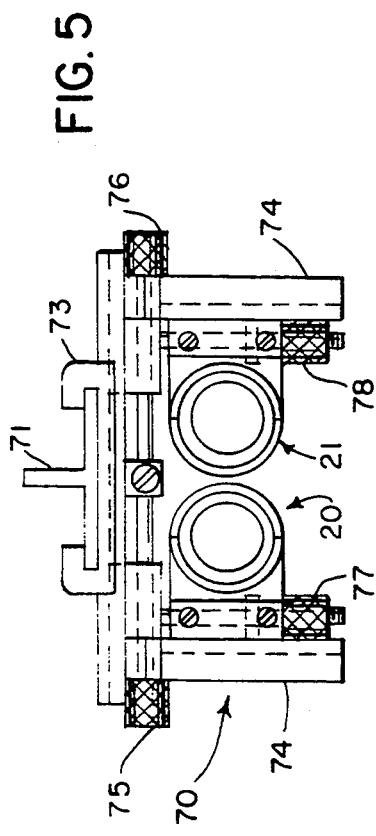
FIG. 5 is an end view of the scopes and their mounting structure shown in FIG. 2.
Figure 2:
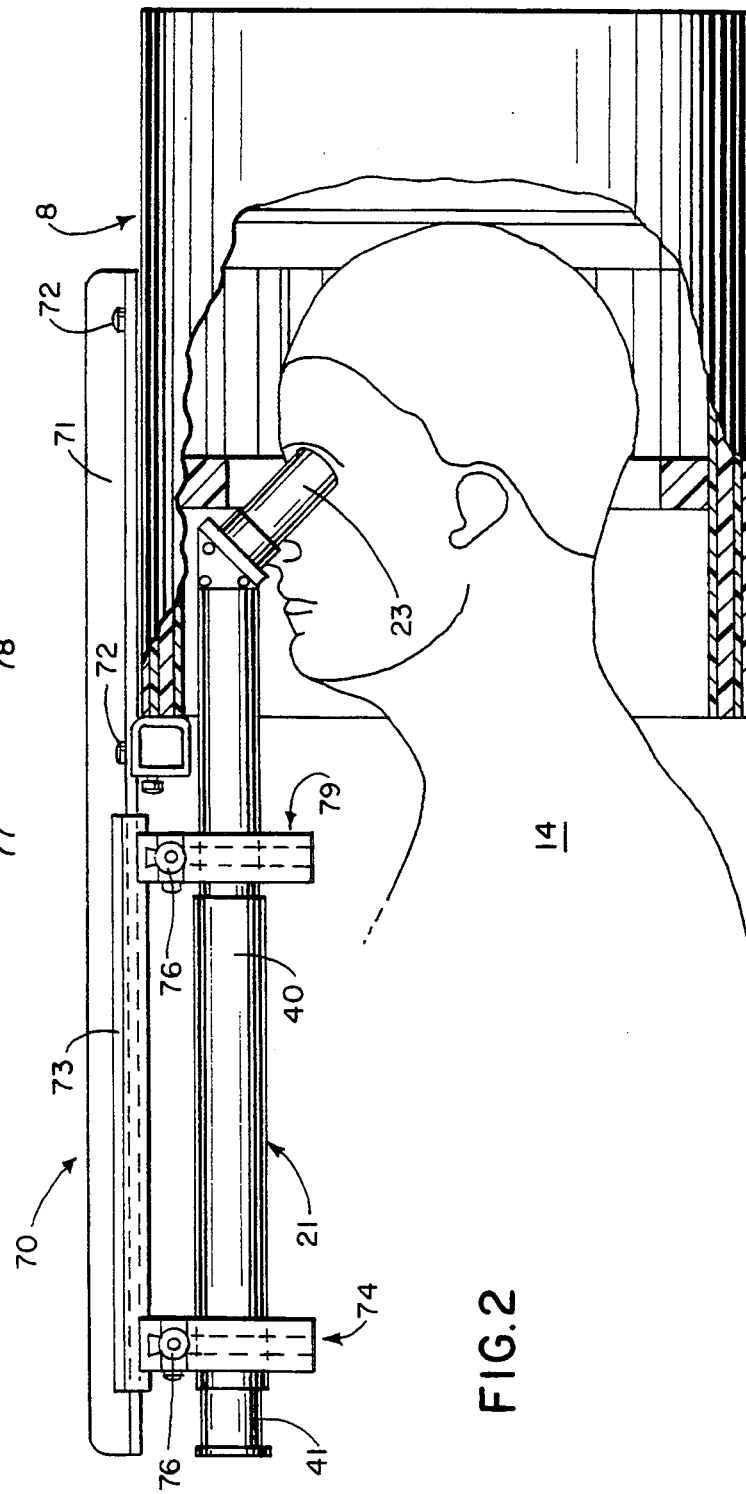
FIG. 2 is a partial view with parts cut away showing a patient positioned in the scanner of FIG. 1.

Referring particularly to FIGS. 2 and 5, the scopes 20 and 21 are supported by a mounting assembly 70 which fastens them to the head coil 8 and positions them as shown over the patient's eyes. The mounting assembly 70 includes a fiberglass support beam 71 which is fastened to the head coil 8 by nylon screws 72. A slidable carriage 73 is carried by the support beam 71 and a forward section 74 extends downward therefrom to separately support the forward end of each scope 20 and 21. By sliding the carriage 73 on the support beam 71, the length of the scopes 20 and 21, and hence their magnification, can be adjusted, and a set of horizontal vernier adjusters 75 and 76 and vertical vernier adjusters 77 and 78 enable the precise location and spacing of the scopes 20 and 21 to be controlled. The slidable carriage 73 also includes a rear section 79 which extends downward therefrom to separately support the scopes 20 and 21 nearer the patient's eyes. The rear section includes the same horizontal and vertical vernier adjustments, however, the tube assembly 40 is slidably supported to enable it to telescope in and out as the carriage 73 is moved on the support beam 71.

The mounting assembly 70 serves to firmly support the scopes 20 and 21 and to provide adjustments of their position and alignment. Adjustments can be made to accommodate variations in the spacing between the patient's eyes, the closeness of the eyepieces 23 to the patient's eyes and the horizontal and vertical registration of the images seen by each eye. And finally, the mounting assembly 70 can be easily detached from the head coil 8 to enable easy patient access to the head coil 8.

Referring particularly to FIG. 4, the display system 30 is constructed by modifying a commercially available LCD video projector identified above. These modifications include removing the lens assembly from the front opening 31 such that the image produced on a reflective surface 50 is seen directly by the patient. In other words, the lens employed to project the image onto a large screen is removed and a pair of variable, crossed polarizing filters 49 are inserted in its place to enable the overall display brightness to be adjusted. The other modification is the addition of a lamp 51 and a monochromator 52 which enables an image produced on LCD 53 to be produced with a precise color. This modification is required for brain function studies that explore how colors are processed by the brain. A monochromator such as the model H-10, commercially available from Instruments SA, Inc. of Metuchen, N.J., may be used for this purpose.

For a conventional color image the display system 30 is operated in its normal manner to produce a red image modulated by LCD 53, a blue image modulated by LCD 54 and a green image modulated by LCD 55. A video controller circuit 56 drives each of the LCDs 53–55 in response to the video signal received at 57 from the computer 32. Only red light from the lamp 51 passes through LCD 53 and a dichroic reflector 60 to the reflector 50 where it is diverted out the opening 31 and contributes to the image seen by the patient 14. Blue light from a lamp 62 passes through a dichroic reflector 63, the LCD 54 and is reflected at 60 and 50 to contribute the blue portions of the image seen by the patient 14. And finally, green light emanating from lamp 62 is reflected at 63, passes through the LCD 55 and is reflected by a reflector 65 towards opening 31. This green image passes through reflector 50 to contribute to the image seen by patient 14. Three lenses 68–70 columnate the light for the respective red, blue and green images.

The resulting image produced in the front opening 31 is approximately a two inch square. Because LCDs and separate light paths are employed for each primary color, the brightness range and color range is much greater than that produced by cathode ray tubes, and the computer control of these parameters is much more precise. While this may not be necessary for many applications, it is required for brain function studies.

The projector 30 is mounted on an adjustable table so that the position of the display can be altered to assist the alignment of the image within the field of view of the scopes 20 and 21. Together with the vernier adjustments on the scope mounting structure, this permits precise alignment of the image in each of the patient's eyes.

In the preferred embodiment the scopes 20 and 21 are each aimed at the 2" square image produced by the display 30 and the entire 60° field of view is filled with the entire image. An alternative embodiment for producing three dimensional images is also possible. In this case, two separate images are produced side-by-side by display 30, and each scope 20 and 21 is aimed at respective ones of the two images. As is well known in the art, small differences in the two images enable the brain to perceive three dimensions, and it is this phenomena which can be explored with great precision using the present invention.

We claim:

1. In a medical imaging system having a bore for receiving a patient while acquiring data from which an image of the patient can be produced, a video system which comprises:
   a scope mounted within the bore of the medical imaging system and having a barrel assembly with an objective lens at one end and an eyepiece at the other end, the eyepiece including a lens which focuses light passing through the objective lens and the barrel assembly on the eye of the patient to enable the patient to look at a remote target area while the data are being acquired by the medical imaging system;
   a display system located remotely from the medical imaging system and including means for producing an image in the target area for the patient to observe through the scope.

2. The video system as recited in claim 1 in which the display system includes a liquid crystal display to produce the image.

3. The video system as recited in claim 2 in which the display system includes three liquid crystal displays to produce images in each of three primary colors that are combined to form the image viewed by the patient.

4. The video system as recited in claim 2 in which light is applied to the liquid crystal display by a lamp and a monochromator is positioned therebetween to control the color of the light.

5. The video system as recited in claim 1 in which the scope includes a second barrel assembly with an objective lens at one end of the second barrel assembly and an eyepiece at the other end of the second barrel assembly, whereby the patient may view the target area separately with each eye.

6. The video system as recited in claim 5 in which the display system includes means for producing two images in the target area, and the two images are seen by the patient through the respective pair of barrel assemblies and associated eyepieces.

7. The video system as recited in claim 1 in which said eyepiece has a focal length such that a focal point of a light path through the scope forms substantially at the pupil of the patient.

8. The video system as recited in claim 7 in which a prism is mounted in the barrel assembly to bend the light path therethrough such that the eyepiece is angled upward from the patient's eye and a central axis of the barrel assembly extends substantially horizontally in the direction of the target area.

9. The video system as recited in claim 8 in which a concave lens is mounted in the barrel assembly between the objective lens and the eyepiece to shorten the distance required therebetween.

* * * * *